United States Patent [19]

Stokbroekx et al.

[11] 4,329,353
[45] May 11, 1982

[54] 1-(4-ARYL-CYCLOHEXYL)PIPERIDINE DERIVATIVES, METHOD OF USE THEREOF AND PHARMACEUTICAL COMPOSITIONS THEREOF

[75] Inventors: Raymond A. Stokbroekx, Beerse; Joannes J. M. Willems, Turnhout; Marcel G. M. Luyckx, Geel, all of Belgium

[73] Assignee: Janssen Pharmaceutica, N.V., Beerse, Belgium

[21] Appl. No.: 222,091

[22] Filed: Jan. 9, 1981

Related U.S. Application Data

[63] Continuation-in-part of Ser. No. 199,142, Oct. 22, 1980, abandoned, which is a continuation-in-part of Ser. No. 128,705, Mar. 10, 1980, abandoned.

[51] Int. Cl.³ ............... A61K 31/445; C07D 471/10; C07D 401/04

[52] U.S. Cl. ...................................... 424/267; 546/20; 546/194; 546/199
[58] Field of Search .............. 546/20, 199, 194; 424/267

[56] References Cited

U.S. PATENT DOCUMENTS

| | | | |
|---|---|---|---|
| 3,759,974 | 9/1973 | Treiber et al. | 260/465 E |
| 4,051,248 | 9/1977 | Vogt et al. | 540/20 |
| 4,076,821 | 2/1978 | Tsuda et al. | 424/263 |

*Primary Examiner*—Robert T. Bond
*Attorney, Agent, or Firm*—Geoffrey G. Dellenbaugh

[57] ABSTRACT

Novel 1-[1-(4-aryl-cyclohexyl)-4-piperidinyl]-1,3-dihydro-2H-benzimidazol-2-ones and 1-aryl-8-(4-aryl-cyclohexyl)-1,3,8-triazaspiro[4,5]decan-4-ones which are useful as antiemetic-and neuroleptic agents.

12 Claims, No Drawings

1-(4-ARYL-CYCLOHEXYL)PIPERIDINE DERIVATIVES, METHOD OF USE THEREOF AND PHARMACEUTICAL COMPOSITIONS THEREOF

CROSS-REFERENCE TO RELATED APPLICATIONS

This is a continuation-in-part of our copending application Ser. No. 199,142, filed Oct. 22, 1980, now abandoned, which in turn is a continuation-in-part of application Ser. No. 128,705, filed Mar. 10, 1980, now abandoned.

BACKGROUND OF THE INVENTION

In U.S. Pat. No. 3,759,974 there are described a number of 4-cyano-4-phenylcyclohexanamines, displaying spasmolytic and neuroleptic activities.

In U.S. Pat. No. 4,076,821 there are described a number of 1-(4,4-diphenylcyclohexyl)piperidines which are useful as long-acting psychotropics, anxiolytics, sedatives, analgetics, CNS-inhibitors, anti-inflammatory agents, coronary vasodilators and hypotensive agents.

In U.S. Pat. No. 4,051,248 there are described a number of 1-phenyl-1,3,8-triazaspiro[4,5]decan-4-ones which are CNS-depressants and neuroleptics used as tranquillizers.

The compounds of the present invention differ from the prior-art compounds by the presence of particular substituents on the cyclohexyl and/or the piperidine ring and/or by their pharmacological activities.

DESCRIPTION OF THE PREFERRED EMBODIMENTS

This invention is concerned with a novel series of 1-(4-arylcyclohexyl)piperidines which may structurally be represented by the formula

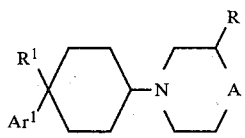

the pharmaceutically acceptable acid addition salts and the stereochemically isomeric forms thereof, wherein
  $Ar^1$ is a member selected from the group consisting of aryl and 1,3-benzodioxolyl;
  R is a member selected from the group consisting of hydrogen and lower alkyl;
  $R^1$ is a member selected from the group consisting of hydrogen, cyano, carboxyl, lower alkyloxycarbonyl, aryllower alkyloxycarbonyl, aminocarbonyl, mono- and di(lower alkyl)aminocarbonyl, mono- and di(aryllower alkyl)aminocarbonyl, (aryllower alkyl)lower alkylamino carbonyl, hydroxy, lower alkyloxy, lower alkylcarbonyloxy, formyl, lower alkylcarbonyl, arylcarbonyl, aryllower alkylcarbonyl, lower alkyl, lower alkenyl, lower alkynyl and cyclohexyl; and
  A is a bivalent radical, having the formula

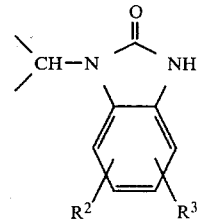

wherein
  $R^2$ and $R^3$ are each independently selected from the group consisting of hydrogen, halo, trifluoromethyl, lower alkyl and lower alkyloxy; or
A is a bivalent radical, having the formula

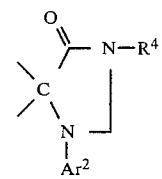

wherein
  $Ar^2$ is aryl, and
  $R^4$ is a member selected from the group consisting of hydrogen, lower alkyl, aryllower alkyl, cyanolower alkyl, aminolower alkyl, mono- and di(lower alkyl)aminolower alkyl, mono- and di(aryllower alkyl)aminolower alkyl, [(aryllower alkyl)lower alkylamino]lower alkyl, hydroxylower alkyl, mercaptolower alkyl, lower alkyloxylower alkyl, lower alkylthiolower alkyl, aryloxylower alkyl, arylthiolower alkyl, aryllower alkyloxylower alkyl, aryllower alkylthiolower alkyl, and a radical of formula

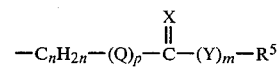

wherein
  n is 0 or an integer of from 1 to 6 inclusive, Q is O, S or $NR^6$, p is 0 or 1, X is O or S, $R^5$ is hydrogen, lower alkyl, aryl or aryllower alkyl, m is 0 or 1 and Y is O, S or $NR^6$, wherein $R^6$ as used in the definition of Q and Y is hydrogen, lower alkyl, aryl or aryllower alkyl;
  provided that when Y is O and m and p are each 1 than $R^5$ is other than hydrogen and provided that when p is 1 than n is other than 0;
wherein aryl is a member selected from the group consisting of phenyl, thienyl, pyridinyl, naphthalenyl and substituted phenyl, said substituted phenyl having from 1 to 3 substituents each independently selected from the group consisting of halo, lower alkyl, lower alkyloxy, phenyl lower alkyloxy, trifluoromethyl, nitro, amino and hydroxy.

As used in the foregoing definitions the term halo is generic to fluoro, chloro, bromo and iodo; the term "lower alkyl" is meant to include straight and branched saturated hydrocarbon radicals having from 1 to 6 carbon atoms such as, for example, methyl, ethyl, 1-methylethyl, 1,1'-dimethylethyl, propyl, 2-methylpropyl, butyl, pentyl, hexyl and the like; "lower alkenyl" and "lower alkynyl" are meant to include straight and branched alkenyl, respectively alkynyl, radicals having from 2 to 6 carbon atoms; the term "cycloalkyl" designates optionally lower alkyl substituted cyclopropyl, cyclobutyl, cyclopentyl, cyclohexyl and cycloheptyl; and "lower alkylene" is meant to include straight or branched saturated lower alkylene radicals.

The compounds of formula (I) can generally be prepared by the reductive amination-reaction of an appropriately substituted cyclohexanone of formula (II), wherein $Ar^1$ and $R^1$ are as previously defined, with an appropriate piperidine derivative of formula (III), wherein A and R are as previously defined.

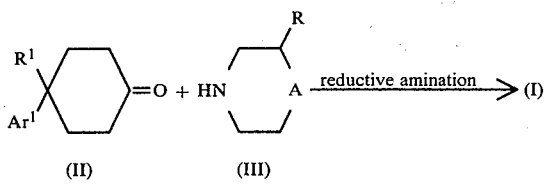

Said reductive amination reaction may conveniently be carried out by catalytically hydrogenating a stirred and heated mixture of the reactants in a suitable reaction-inert organic solvent according to art-known catalytically hydrogenating procedures. Suitable solvents are, for example, water; lower alkanols, e.g., methanol, 2-propanol and the like; cyclic ethers, e.g., 1,4-dioxane and the like; halogenated hydrocarbons, e.g., trichloromethane and the like; N,N-dimethylformamide; dimethyl sulfoxide and the like; or a mixture of 2 or more of such solvents. The term "art-known catalytically hydrogenating procedures" means that the reaction is carried out under hydrogen atmosphere and in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalystpoison to the reaction-mixture, e.g., thiophene and the like.

The compounds of formula (I) may also be prepared by reacting the cyclohexanone (II) with the piperidine (III) and reducing the intermediately formed enamine of formula (IV).

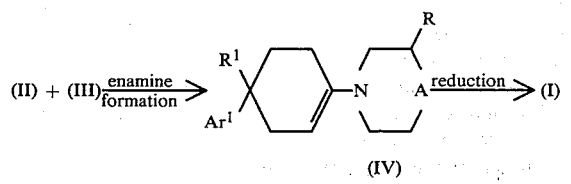

The enamine formation reaction may be carried out by stirring the reactants together in the presence of a catalytic amount of a relatively strong acid, e.g., 4-methylbenzenesulfonic acid and the like, in a suitable reaction-inert organic solvent such as, for example, an aliphatic-, alicyclic- or aromatic hydrocarbon, e.g., n. hexane, cyclohexane, methylbenzene and the like. In order to enhance the reaction rate somewhat elevated temperatures are appropriate and preferably the reaction is conducted at the reflux temperature of the reaction mixture. Most preferably the reaction is carried out under azeotropic removal of the water which is formed during the course of the reaction.

The reduction of the enamine of formula (IV) may, for example, be carried out by stirring the enamine (IV) in a suitable solvent in the presence of an appropriate reducing agent such as, for example, a complex metal hydride, e.g., sodium borohydride and the like. Suitable solvents are, for example, alkanols, e.g., methanol, 2-propanol and the like; and cyclic ethers, e.g., tetrahydrofuran, 1,4-dioxane and the like; if desired, in admixture with water. Elevated temperatures may be used to enhance the rate of the reaction. In order to avoid the undesired decomposition of the reducing agent it may be advantageous to carry out the reaction in alkaline medium, e.g., sodium methoxide in methanol, sodium hydroxide in water and the like.

The compounds of formula (I) may also be prepared by reacting an appropriate cyclohexane of formula (V), wherein $R^1$ and $Ar^1$ are as previously described and wherein W represents an appropriate reactive leaving group such as, for example, halo, preferably chloro, bromo or iodo, or a sulfonyloxy group, e.g., methylsulfonyloxy, 4-methylphenylsulfonyloxy and the like, with an appropriately substituted piperidine of formula (III) following art-known N-alkylating procedures.

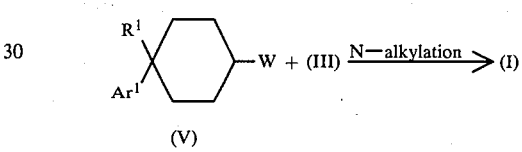

Said N-alkylation-reaction is conveniently conducted in an inert organic solvent such as, for example, an aromatic hydrocarbon, e.g., benzene, methylbenzene, dimethylbenzene and the like; a lower alkanol, e.g., methanol, ethanol, 1-butanol and the like; a ketone, e.g., 4-methyl-2-pentanone and the like; an ether, e.g., 1,4-dioxane, 1,1'-oxybisethane and the like; N,N-dimethylformamide; nitrobenzene and the like.

The addition of an appropriate base such as, for example, an alkali metal carbonate or hydrogen carbonate, or an organic base such as, for example, N,N-diethylethanamine and the like may be utilized to pick up the acid which is liberated during the course of the reaction. In certain cases the addition of an iodide salt, preferably an alkali metal iodide, is appropriate. Somewhat elevated temperatures may be used to enhance the reaction rate.

Depending upon the nature of $R^1$ the compounds of formula (I) can be converted into each other following art-known procedures of functional group transformation. Some functional group transformations are illustrated in scheme 1 wherein the radical

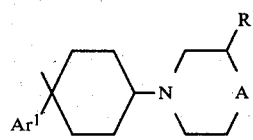

is represented by L.

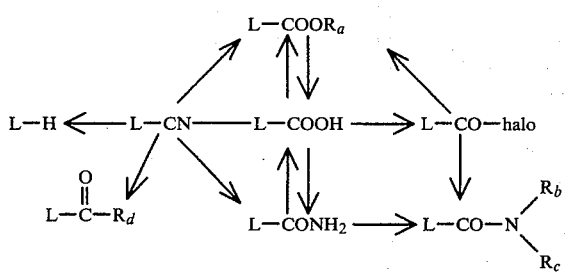

scheme 1

In scheme 1 $R_a$ is lower alkyl or aryllower alkyl, $R_b$ is hydrogen, lower alkyl or aryllower alkyl, $R_c$ is lower alkyl or aryllower alkyl and $R_d$ is hydrogen, lower alkyl, aryl or aryllower alkyl.

The nitrile function may be converted into a hydrogen radical following art-known reductive decyanation procedures as described, for example, in J. Am. Chem. Soc., 56, 1614–1616 (1934) and J. Am. Chem. Soc., 91, 2059–2062 (1969), by stirring and heating the nitriles with sodium or sodium amide in the presence of a high boiling hydrocarbon, e.g., methylbenzene and the like.

The nitrile function may also be converted into an aminocarbonyl function by hydrolyzing the nitrile in strong acidic medium. The thus obtained aminocarbonyl compound may further be hydrolyzed in weak acidic aqueous medium, thus yielding the corresponding carboxylic acid. The carboxylic acid may be derived directly from the nitrile by hydrolyzing the latter in weak acidic aqueous medium, while the ester may be derived from the nitrile by alcoholyzing the starting nitrile.

The carboxylic function may be converted into an ester function, an amide function or a halocarbonyl function following art-known procedures, e.g., by stirring and, if desired, heating and starting carboxylic acid with an appropriate alcohol, respectively an amine and a halogenating agent. Appropriate halogenating agents are, for example, phosphoryl chloride, phosphorpentabromide, thionyl chloride and the like. The carboxylic acid function may also be converted into an ester function by reacting the starting carboxylic acid with an appropriate alkyl halide or aryllower alkyl halide in the presence of a base, e.g., sodium methoxide and the like.

The halocarbonyl function may be converted into an amide function or an ester function by stirring and, if desired, heating the starting halocarbonyl compound with an appropriate amine, respectively an appropriate alcohol. The ester- and amide function may be converted into a carboxyl function following art-known hydrolyzing procedures, e.g., by stirring and heating the starting ester in acidic or alkaline aqueous medium.

The secondary and tertiary amide functions may be prepared by N-alkylating an primary amide, respectively a secondary amide compound, following art-known N-alkylating procedures.

The cyanide function may be converted into a formyl function following art-known reducing procedures, e.g., by stirring the starting nitrile compound in the presence of lithium aluminium hydride or lithium triethoxyhydroaluminate in a suitable solvent such as 1,1'-oxybisethane and the like.

The lower alkylcarbonyl-, arylcarbonyl- and aryllower alkylcarbonyl functions may be derived from the nitrile function by reacting the starting nitrile with an appropriate lower alkyl halide, aryl halide or aryllower alkyl halide in the presence of magnesium following art-known Grignard reaction procedures.

The compounds of formula (I) wherein A is the radical (b) and wherein $R^4$ is hydrogen, said compounds being represented by the formula (I-a), can be converted into the compounds of formula (I) wherein A is the radical (b) and wherein $R^4$ is other than hydrogen, said $R^4$ being represented by $R^{4-a}$ and said compounds by the formula (I-b).

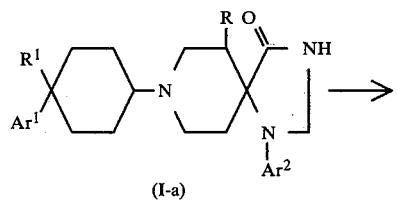

The compounds of formula (I-b), wherein $R^{4-a}$ is as previously described, provided that in the radical

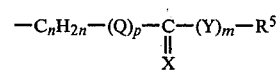

n is not 0, said $R^{4-a}$ being represented by $R^{4-a-1}$ and said compounds by the formula (I-b-1), can be prepared by reacting an appropriate compound of formula (I-a) with a reagent of formula (VI) following art-known N-alkylating procedures as previously described for the reaction of (V) with (III).

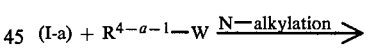

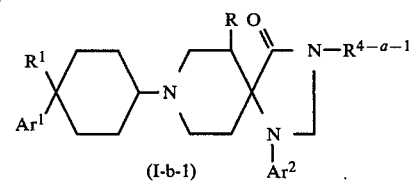

The compounds of formula (I-b) wherein $R^{4-a}$ represents a radical having the formula

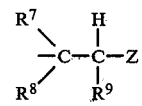

wherein $R^7$, $R^8$ and $R^9$ are each, independently from each other, hydrogen or lower alkyl, provided that their sum does not exceed 4 carbon atoms, and Z is cyano or a radical of formula

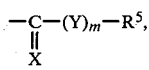

said compounds being represented by the formula (I-b-2), can also be prepared by the 1,4-addition reaction of a reagent of formula (VII) to a compound of formula (I-a).

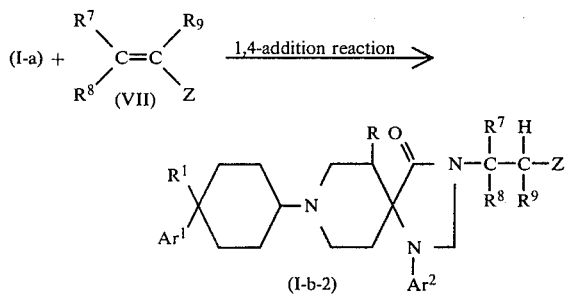

The 1,4-addition reaction may generally be carried out by stirring and, preferably, heating the reactants together in a suitable solvent such as, for example, an ether, e.g., 1,4-dioxane, tetrahydrofuran and the like, an alcohol, e.g., methanol, 2-propanol and the like, an aliphatic-, alicyclic- or aromatic hydrocarbon, e.g., cyclohexane, pentane, methylbenzene and the like, in the presence of a suitable base, e.g., N,N,N-trimethylbenzenemethanaminium hydroxide and the like.

The compounds of formula (I-b) wherein $R^{4-a}$ represents a radical having the formula

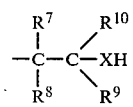

wherein $R^7$, $R^8$, $R^9$ and $R^{10}$ are each, independently from each other, hydrogen or lower alkyl, provided that their sum does not exceed 4 carbon atoms, and X is O or S, said compounds being represented by the formula (I-b-3), may also be prepared by reacting a compound of formula (I-a) with a reagent of formula (VIII) following art-known N-alkylating procedures.

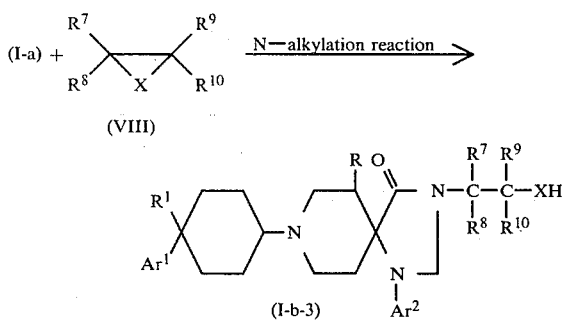

The compounds of formula (I-b) wherein $R^{4-a}$ represents a radical of formula

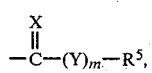

provided that $R^5$ is other than hydrogen, said $R^5$ being represented by $R^{5-a}$ and said compounds by the formula (I-b-4), may also be prepared by reacting a compound of formula (I-a) with a reagent of formula (IX) wherein halo is chloro, bromo or iodo, following art-known N-acylating procedures, by stirring and heating the reactants together in the presence of a reaction-inert solvent such as, for example, ethers, e.g., 1,4-dioxane, tetrahydrofuran and the like, aliphatic-, alicyclic- and aromatic hydrocarbons, e.g., pentane, cyclohexane, methylbenzene and the like.

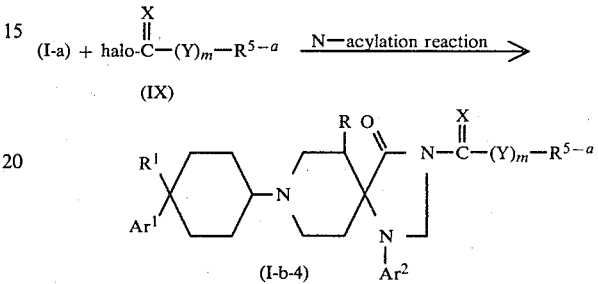

The compounds of formula (I-b) wherein $R^{4-a}$ represents a radical of formula

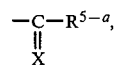

said compounds being represented by the formula (I-b-5), can also be prepared by reacting a compound of formula (I-a) with a reagent of formula (X).

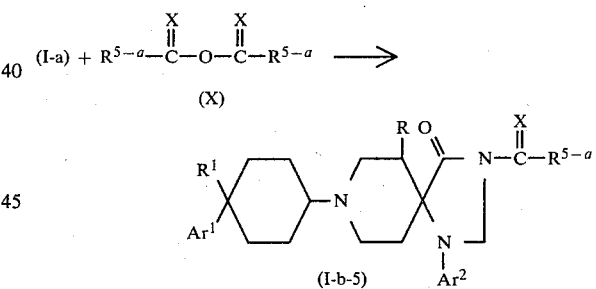

This reaction may be carried out by stirring and, if desired, heating the reactants together in a suitable reaction-inert solvent, e.g., methylbenzene and the like, preferably in the presence of an appropriate acid, e.g., 4-methylbenzenesulfamic acid and the like.

The compounds of formula (I-b) wherein $R^{4-a}$ represents a radical of formula

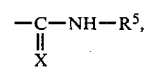

said compounds being represented by the formula (I-b-6), may also be prepared by reacting a compound of formula (XI) by stirring and, if desired, heating the reactants together in the presence of a suitable solvent, e.g., methylbenzene and the like, in the presence of an appropriate base, e.g., N,N-dimethyl-4-pyridinamine.

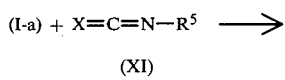

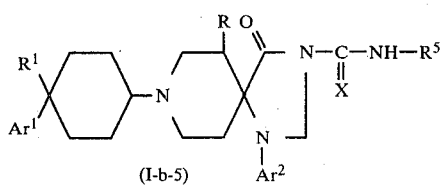

The compounds of formula (I) may be converted to the therapeutically active non-toxic acid addition salt forms by treatment with an appropriate acid, such as, for example, an inorganic acid, such as hydrohalic acid, e.g., hydrochloric, hydrobromic and the like, and sulfuric acid, nitric acid, phosphoric acid and the like; or an organic acid, such as, for example, acetic propanoic, 2-hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Conversely the salt form can be converted by treatment with alkali into the free base form.

It is obvious from formula (I) that the compounds of this invention may exist under different stereochemically isomeric forms.

Due to the substitution on the cyclohexyl ring said compounds may be present in two different geometrically isomeric forms, namely cis- and trans-form.

Moreover, when R represents a lower alkyl radical, two additional asymmetric carbon atoms are present. Each of these chiral centers may be present in an R- and an S-configuration, this R- and S-notation being in correspondence with the rules described by R. S. Cahn, C. Ingold and V. Prelog in Angew. Chem., Int. Ed. Engl., 5, 385, 511 (1966). Due to the 2 asymmetric carbon atoms the piperidine moiety may be present in a cis- and a trans form.

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occur stereospecifically.

In most compounds and starting materials the stereochemical configuration is not experimentally determined. In those cases it is conventionally agreed to designate the stereochemically isomeric form which is first isolated as "A" and the second as "B", without further reference to the actual stereochemical configuration. The suffix p or c indicate the piperidine-, respectively cyclohexyl moiety the stereochemical notation is related to.

Stereochemically isomeric forms of the compounds of formula (I) are naturally intended to be embraced within the scope of the invention.

A large number of intermediates and starting materials in the foregoing preparations are known compounds and all of them may be prepared according to art-known methodologies of preparing similar compounds. A number of such preparation methods will be described hereafter in somewhat more detail.

The intermediates of formula (II) may be prepared by a Michael-addition reaction of an appropriate arylacetonitrile (XII) with a propenoic acid ester (XIII), wherein $R^{11}$ represents an optionally substituted lower alkyl radical, and subsequent hydrolysis of the thus obtained cyclic Michael addition reaction product in acidic medium.

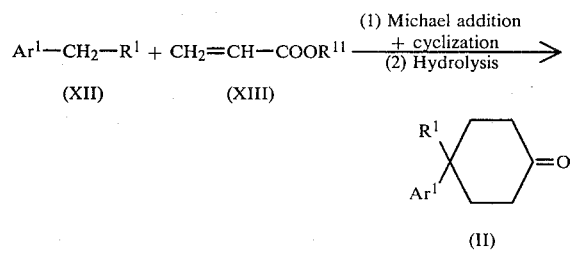

Said Michael addition reaction is conveniently conducted by stirring and, if desired, heating the reactants together in a suitable solvent such as, for example, an alkanol, e.g., ethanol, 1,1-dimethylethanol and the like; an aliphatic-, alicyclic- or aromatic hydrocarbon, e.g., n-hexane, cyclohexane, methylbenzene and the like; in the presence of an appropriate strong base, e.g., sodium hydride, sodium methoxide and the like, depending upon the solvent used. Preferably the reaction is conducted at the reflux temperature of the reaction mixture.

The hydrolysis is generally carried out by stirring and heating the Michael addition reaction product in aqueous acidic medium, e.g., aqueous hydrochloric acid and the like.

The intermediates of formula (V) may be prepared by converting the hydroxyl function of an appropriately substituted cyclohexanol (XIV) into an appropriate reactive leaving group W.

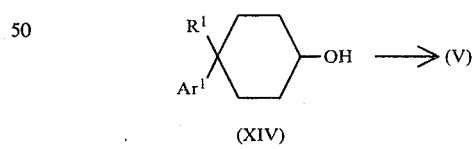

Said conversion of the hydroxylfunction into a leaving group W may, for example, be carried out by stirring the alcohol (XIV) with an appropriate halogenating- or sulfonylating agent, e.g., thionyl chloride, methanesulfonyl chloride and the like. In order to neutralize the acid which is liberated during the course of the reaction it may be appropriate to add an appropriate base to the reaction mixture or to carry out the reaction in a suitable alkaline organic solvent, e.g., pyridine and the like.

The cyclohexanol (XIV) can be derived from the corresponding cyclohexanone (II) following art-known reducing procedures.

Depending upon the nature of $R^1$ the intermediates (II) and (V) can be converted into each other following art-known procedures of functional group transformation, as illustrated in scheme 1. In some cases it may be advantageous that, before the functional grouptransformation is carried out, other functions, which are present in the starting intermediate, are protected and that, afterwards, the protective groups are eliminated.

A number of intermediates of formula (III) are described in U.S. Pat. Nos. 3,929,801 and 3,155,670 and in Helv. Chim. Acta 1960, 1298–1313 and all of them may be prepared following analogous procedures.

The compounds of formula (I), their pharmaceutically acceptable acid-addition salts and the geometrically isomeric forms thereof possess strong psychotropic and antiemetic activity. Such psychotropic and antiemetic activity is evidenced by the experimental data obtained in at least one of two different test procedures, viz., the combined apomorphine-, tryptamine- and norepinephrine tests in rats and the apomorphine test in dogs. The tests were carried out following the procedures described hereafter and the experimental data which were obtained are summarized in the tables 1, 2 and 3.

I. The combined apomorphine (APO)-, tryptamine (TRY)- and norepinephrine (NOR) test in rats.

The experimental animals used in this test were adult male Wistar rats (weight 240±10 g). After an overnight fast, the animals were treated subcutaneously (1 ml/100 g) with an aqueous solution of the compound under investigation (time=zero) and put in isolated observation cages. Thirty minutes thereafter (time=30 minutes) 1.25 mg/kg of apomorphine hydrochloride (APO) was injected intravenously and the rats were observed over a 1 hour period for the presence or absence of the following apomorphine-induced phenomena: agitation and stereotypic chewing. At the end of this 1 hour period (time=90 minutes) the same animals were injected intravenously with 40 mg/kg of tryptamine (TRY) and the presence of the typical tryptamine-induced bilateral tonic seizures was noted. Two hours after pretreatment (time=120 minutes) finally, the same animals were challenged with 1.25 mg/kg intravenously of norephinephrine (NOR) and possible mortality was looked for up to 60 minutes later.

The tables 1, 2 and 3 give the $ED_{50}$-values of a number of the compounds under consideration. As used herein, the $ED_{50}$-value represents the dose which protects 50% of the animals from apomorphine-, tryptamine- or norepinephrine-induced phenomena.

2. The apomorphine test in dogs (APO-dog).

The method used is described by P.A.J. Janssen and C.J.E. Niemegeers in Arzneim.-Forsch. (Drug Res), 9, 765–767 (1959).

The compounds listed in tables 1, 2 and 3 were administered subcutaneously to beagle dogs at different doses and the animals were challenged 1 hour thereafter with a standard dose of 0.31 mg/kg (subcutaneous) of apomorphine.

The tables 1, 2 and 3 give the $ED_{50}$-values of a number of the compounds under consideration. As used herein, the $ED_{50}$-value represents the dose which protects 50% of the animals from emesis.

It is understood that the compounds shown in the tables 1, 2 and 3 are not listed for the purpose of limiting the invention thereto, but only to exemplify the outstanding antiemetic- and psychotropic properties of all the compounds within the scope of formula (I).

TABLE 1

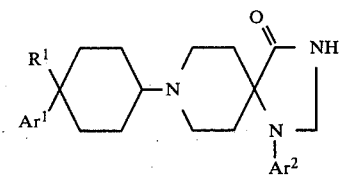

| $R^1$ | $Ar^1$ | $Ar^2$ | geometric isomer | base or salt | $ED_{50}$(APO)-rat in mg/kg s.c. | $ED_{50}$(TRY) in mg/kg s.c. | $ED_{50}$(NOR) in mg/kg s.c. | $ED_{50}$(APO)dog in mg/kg s.c. |
|---|---|---|---|---|---|---|---|---|
| CN | $C_6H_5$ | $C_6H_5$ | | base | <10 | — | — | 0.001 |
| CN | 4-Cl—$C_6H_4$ | $C_6H_5$ | | base | 5.0 | — | — | 0.007 |
| CN | 4-F—$C_6H_4$ | $C_6H_5$ | | base | 0.16 | — | 10 | 0.0005 |
| CN | 4-$OCH_3$—$C_6H_4$ | $C_6H_5$ | | base | 10 | — | — | 0.002 |
| $COOC_2H_5$ | 4-F—$C_6H_4$ | $C_6H_5$ | | base | 0.31 | 2.5 | 10 | 0.007 |
| CN | $C_6H_5$ | $C_6H_5$ | B | base | 0.08 | 2.0 | — | 0.00063 |
| $COOC_2H_5$ | $C_6H_5$ | 4-F—$C_6H_4$ | | base | 1.25 | 5 | — | 0.009 |
| $COOC_2H_5$ | 4-F—$C_6H_4$ | 4-F—$C_6H_4$ | | base | 2.5 | 5 | <2.5 | 0.003 |
| $COOCH_3$ | 4-F—$C_6H_4$ | 4-F—$C_6H_4$ | | base | — | — | — | 0.0018 |
| $CONH_2$ | 4-F—$C_6H_4$ | 4-F—$C_6H_4$ | B | base | — | — | — | 0.008 |
| COOn.$C_4H_9$ | 4-F—$C_6H_4$ | 4-F—$C_6H_4$ | A—B | base | 10 | — | 1.25 | 0.008 |
| $OCH_3$ | 4-F—$C_6H_4$ | 4-F—$C_6H_4$ | A—B | base | 0.63 | 5 | 2.5 | 0.03 |
| COOn.$C_3H_7$ | 4-F—$C_6H_4$ | 4-F—$C_6H_4$ | A—B | base | 5 | 10 | 1.25 | 0.008 |
| $COCH_3$ | 4-F—$C_6H_4$ | 4-F—$C_6H_4$ | B | HCl | 2.5 | — | 10 | 0.03 |

TABLE 2

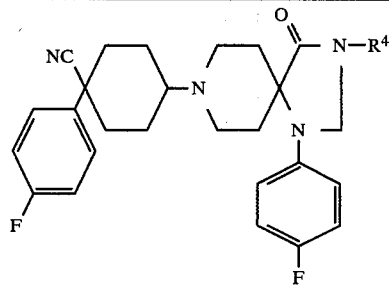

| R⁴ | geometric isomer | base/salt | ED$_{50}$(APO)-rat in mg/kg s.c. | ED$_{50}$-(TRY) in mg/kg s.c. | ED$_{50}$-(NOR) in mg/kg s.c. | ED$_{50}$(APO)-dog in mg/kg |
|---|---|---|---|---|---|---|
| CH$_2$CH$_2$CN | B | base | 0.16 | 1.25 | 5 | 0.0005 |
| CH$_2$CH$_2$COOCH$_3$ | B | HCl | 0.63 | 10 | — | 0.002 |
| CH$_3$ | B | base | 0.04 | 0.08 | — | 0.001 |
| CH$_2$CH(CH$_3$)CN | B | base | 0.16 | 0.31 | — | 0.0005 |
| CH(CH$_3$)CH$_2$COOCH$_3$ | B | HCl | 5 | 10 | — | 0.002 |
| CH$_2$C$_6$H$_5$ | | base | — | — | 10 | 0.008 |
| CH$_2$CH$_2$COCH$_3$ | B | HCl · H$_2$O | — | — | — | 0.002 |
| CH$_2$CH(CH$_3$)COOCH$_3$ | B | HCl | <10 | <10 | 10 | 0.001 |
| CH(CH$_3$)CH$_3$ | B | base | <10 | <10 | 10 | 0.001 |
| CS—NH—CH$_3$ | | base | — | — | — | <0.004 |
| CO—NH—C$_6$H$_5$ | B | base | — | — | — | <0.16 |
| CH$_2$—CO—NH$_2$ | B | base | — | — | 1.25 | 0.0009 |
| CH$_2$—CO—NH—CH$_3$ | B | HCl | — | 5 | ≦2.5 | 0.0016 |
| CH$_2$—CO—N(CH$_3$)$_2$ | B | HCl | <2.5 | <2.5 | 5 | 0.001 |

TABLE 3

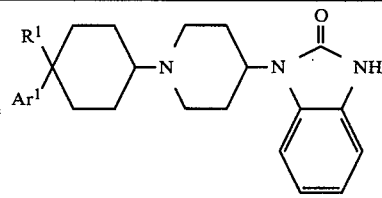

| R¹ | Ar¹ | geometric isomer | base/salt | ED$_{50}$(APO)-rat in mg/kg s.c. | ED$_{50}$-(TRY) in mg/kg s.c. | ED$_{50}$-(NOR) in mg/kg s.c. | ED$_{50}$-(APO)-dog in mg/kg s.c. |
|---|---|---|---|---|---|---|---|
| CN | 4-F—C$_6$H$_4$ | — | base | 0.16 | — | 0.31 | 0.15 |
| CN | 4-Cl—C$_6$H$_4$ | — | base | 2.5 | — | 0.31 | >0.04 |
| CON(CH$_3$)$_2$ | 4-F—C$_6$H$_4$ | — | CH$_3$—CH(OH)—CH$_3$ | — | — | 1.25 | — |
| COOC$_2$H$_5$ | 4-F—C$_6$H$_4$ | — | HCl | 0.31 | 5 | 2.5 | 0.04 |
| CN | C$_6$H$_5$ | — | HCl | 1.25 | — | 1.25 | 0.06 |
| CON(CH$_3$)$_2$ | 4-OCH$_3$—C$_6$H$_4$ | — | HCl · H$_2$O | — | — | 5 | — |
| COOC$_2$H$_5$ | C$_6$H$_5$ | — | base | 1.25 | 5 | 1.25 | 0.25 |

In view of their antiemetic and psychotropic activity, the subject compounds may be formulated into various pharmaceutical forms for administration purposes. To prepare the pharmaceutical compositions of this invention, an effective antiemetic or psychotropic amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following formulations exemplify typical antiemetic and psychotropic pharmaceutical compositions in dosage unit form suitable for systemic administration to animal and human subjects in accordance with the instant invention.

Oral drop: The following formulation provides 10 liters of an oral-drop solution comprising 5 milligrams of (B)-1-(4-fluorophenyl)4-[1-(4-fluorophenyl)-4-oxo-1,3,8-triazaspiro[4,5]decan-8-yl]cyclohexanecarbonitrile as the active ingredient per ml.

| A.I. | 50 grams |
|---|---|
| 2-Hydroxypropanoic acid | 2.5 milliliters |
| Methyl 4-hydroxybenzoate | 18 grams |
| Propyl 4-hydroxybenzoate | 2 grams |
| Pyrogen-free water q.s. ad 10 liters. | |

The methyl and propyl 4-hydroxybenzoates are dissolved in about 5 liters of boiling pyrogen-free water. After cooling to about 50° C. there are added while stirring the 2-hydroxypropanoic acid and thereafter the A.I. The solution is cooled to room temperature and supplemented with pyrogen-free water ad volume. The solution is sterilized by filtration (U.S.P. XVII p. 811) and filled in sterile containers.

Injectable solution: The oral drop solution described herebefore may be used as an injectable solution.

Capsules: 10,000 Hard gelatine capsules, each containing as the active ingredient (A.I.) 20 milligrams of (B)-1-(4-fluorophenyl)-4-[I-(4-fluorophenyl)-4-oxo-1,3,8-triazaspiro[4,5]-decan-8-yl]cyclohexanecarbonitrile, are prepared from the following composition.

| A.I. | 200 grams |
|---|---|
| Lactose | 1000 grams |
| Starch | 300 grams |
| Talc | 300 grams |
| Calcium stearate | 10 grams |

An uniform mixture of the active and supplementary ingredients is prepared and filled into two-piece hard gelatine capsules.

Tablets: 5000 Compressed tablets, each containing as the active ingredient (A.I.) 25 milligrams of (B)-1-(4-fluorophenyl)-4-[1-(4-fluorophenyl)-4-oxo-1,3,8-triazaspiro[4,5]decan-8-yl]cyclohexanecarbonitrile, are prepared from the following formulation.

| A.I. | 125 grams |
|---|---|
| Starch | 150 grams |
| Dibasic calcium phosphate hydrous | 650 grams |
| Calcium stearate | 35 grams |

The finely powdered ingredients are mixed well and granulated with 10% starch paste. The granulation is dried and compressed into tablets.

Oral suspension: The following formulation provides 5 liters of an oral suspension comprising as an active ingredient (A.I.) 15 milligrams of (B)-1-(4-fluorophenyl)-4-[1-(4-fluorophenyl)-4-oxo-1,3,8-triazaspiro[4,5]decan-8-yl]cyclohexanecarbonitrile per teaspoonfull (5 milliliters).

| A.I. | 15.0 | grams |
|---|---|---|
| Sucrose | 300.0 | grams |
| Dioctyl sodium sulfosuccinate | 0.5 | grams |
| Bentonite | 22.5 | grams |
| Methyl paraben | 7.5 | grams |
| Propyl paraben | 1.5 | grams |
| Antifoam A.F. Emulsion | 0.15 | grams |
| Propylene Glycol | 52.0 | grams |
| FD & C Yellow #5 | 0.1 | grams |
| Sodium cyclamate | 50.0 | grams |
| Sodium saccharin | 5.0 | grams |
| Orange flavor | 7.5 | grams |
| Filtered purified water, q.s., ad | 5 | liters. |

Dissolve the parabens in the propylene glycol and add this solution to a solution of the sodium cyclamate, sodium saccharin and sucrose in half the water. Suspend the bentonite in hot (about 85° C.) water and stir for 60 minutes. Add the bentonite solution to the former solution. Dissolve the sulfosuccinate in some water and suspend the A.I. in the resulting solution. Add the Antifoam A.F. Emulsion which has been diluted to a lotion consistency with a minimum amount of water and mix well. Add the latter suspension of A.I. to the former mixture and mix well. Add the FDC Yellow #5 dissolved in a small amount of water. Add the orange flavor, q.s. to volume with water, and stir to a homogeneous mixture. Pass the mixture through a colloid mill and fill into suitable containers.

In view of the antiemetic activity of the subject compounds, it is evident that the present invention provides a method of inhibiting emesis in warm-blooded animals affected by emesis, by the systemic administration of an effective antiemetic amount of a compound of formula (I) and the pharmaceutically acceptable acid addition salts thereof in admixture with a pharmaceutical carrier.

In addition, in view of the psychotropic activity of the subject compounds, the present invention also provides a method of treating mental disorders in warm-blooded animals affected by such disorders, by the systemic administration of an effective psychotropic inhibiting amount of a compound of formula (I) and the pharmaceutically acceptable acid addition salts thereof in admixture with a pharmaceutical carrier.

The following examples are intended to illustrate but not to limit the scope of the present invention. Unless otherwise stated all parts therein are by weight.

EXAMPLES

A. Preparation of Intermediates

Example I

75 Parts of ethyl 4-oxo-1-piperidinecarboxylate and 50 parts of 4-fluorobenzeneamine are added dropwise to 220 parts of acetic acid. The whole is stirred for 30 minutes. Then there is added dropwise a solution of 23 parts of sodium cyanide in 65 parts of water at room temperature (exothermic reaction). Upon completion, a second portion of 2 parts of sodium cyanide is added and the whole is stirred overnight. The reaction mixture is poured onto a mixture of 440 parts of water, 440 parts of ammonium hydroxide solution and 525 parts of trichloromethane. The trichloromethane-phase is separated and the aqueous layer is extracted with trichloromethane. The combined organic layers are washed with water, dried and evaporated, yielding 127.5 parts of ethyl 4-cyano-4-(4-fluorophenylamino)-1-piperidinecarboxylate as a residue.

127.5 parts of ethyl 4-cyano-4-(4-fluorophenylamino)-1-piperidinecarboxylate are added dropwise to 360 parts of concentrated sulfuric acid (exothermic reaction: temperature rises to 50° C.). Upon completion, the whole is stirred overnight at room temperature. The reaction mixture is poured onto crushed ice and 250 parts of water are added. The whole is alkalized with sodium hydroxide solution at a temperature of 40°–50° C., whereupon the product is precipitated. It is filtered off, washed with water and taken up in boiling trichloromethane. The latter is washed twice with water, dried and evaporated, yielding 82.1 parts of less pure ethyl 4-carbamoyl-4-(4-fluorophenylamino)-1-piperidinecarboxylate.

A sample of 2 parts is crystallized from absolute ethanol, yielding 1 part of ethyl 4-carbamoyl-4-(4-fluorophenylamino)-1-piperidinecarboxylate; mp. 187° C.

To a solution of 6.9 parts of paraformaldehyde in 100 parts of N,N-dimethylformamide are added portionwise 46.3 parts of ethyl 4-carbamoyl-4-(4-fluorophenylamino)-1-piperidinecarboxylate. The whole is stirred and refluxed for 20 hours. Then 50 parts of the solvent are distilled off (t°: 142°–152° C.). A second portion of 1 part of paraformaldehyde in 50 parts of N,N-dimethylformamide is added and stirring and refluxing is continued for 48 hours. The N,N-dimethylformamide is distilled off to a volume of about 50 parts and the distillate is poured onto water. The water is decanted and the residue is extracted with trichloromethane. The extract is washed with water, dried, filtered and evaporated. The residue is triturated in 2,2'-oxybispropane. The product is filtered off and crystallized from a mixture of benzene and 2,2'-oxybispropane, yielding 17.5 parts of ethyl 1-(4-fluorophenyl)-4-oxo-1,3,8-triazaspiro[4,5]decane-8-carboxylate; mp. 153° C.

Example II

To a stirred solution of 248 parts of methyl 3-methyl-4-oxo-1-piperidinecarboxylate in 660 parts of acetic acid are added 150 parts of 4-fluorobenzenamine and the whole is stirred for 30 minutes. After cooling with ice-water, a solution of 69 parts of sodium cyanide in 195 parts of water is added dropwise at room temperature. Upon completion, stirring at room temperature is continued over week-end. The solid product is filtered off and washed with 2,2'-oxybispropane and petroleumether, yielding 230 parts of methyl 4-cyano-4-[(4-fluorophenyl)amino]-3-methyl-1-piperidinecarboxylate; mp. 90° C.

To 1800 parts of concentrated sulfuric acid are added portionwise 320 parts of methyl 4-cyano-4-[(4-fluorophenyl)amino]-3-methyl-1-piperidinecarboxylate, while the temperature is allowed to reach 50° C. Upon completion, stirring is continued first for 5 hours at 50° C. and further overnight while meantime the mixture is allowed to cool to room temperature. The reaction mixture is poured onto crushed ice, alkalized with a concentrated ammonium hydroxide solution at a temperature below 40° C., and the product is extracted with trichloromethane. The extract is washed with water, dried, filtered and evaporated. The semi-solid residue is boiled in 400 parts of 2-propanone.

1. After cooling to room temperature, the undissolved product is filtered off (the filtrate is set aside) and boiled in 400 parts of acetonitrile. After cooling to room temperature, the product is filtered off and boiled in 1200 parts of 2-propanol. The undissolved part is filtered off and discarded. After cooling the filtrate, the product is precipitated. It is filtered off and dried, yielding 21.3 parts of B-methyl 4-(aminocarbonyl)-4-[(4-fluorophenyl)amino]-3-methyl-1-piperidinecarboxylate; mp. 223.5° C.

2. From the filtrate, which was set aside (see sub. 1), a product is precipitated. It is filtered off and crystallized from 160 parts of acetonitrile, yielding 20.5 parts of A-methyl-4-(aminocarbonyl)-4-[(4-fluorophenyl)amino]-3-methyl-1-piperidinecarboxylate; mp. 189.5° C.

Example III

A mixture of 22.3 parts of A-methyl 4-(aminocarbonyl)-4-[(4-fluorophenyl)amino]-3-methyl-1-piperidinecarboxylate, 86 parts of a formaldehyde solution 40% and 47 parts of N,N-dimethylformamide is stirred and refluxed for 3 days. The reaction mixture is evaporated in vacuo. The residue is dissolved in methylbenzene and water. The methylbenzene-phase is separated, washed with water, dried, filtered and evaporated, yielding 27 parts of A-methyl 1-(4-fluorophenyl)-3-(hydroxymethyl)-6-methyl-4-oxo-1,3,8-triazaspiro[4,5]-decane-8-carboxylate as an oily residue.

In a similar manner there is also prepared:
B-methyl 1-(4-fluorophenyl)-3-(hydroxymethyl)-6-methyl-4-oxo-1,3,8-triazaspiro[4,5]decane-8-carboxylate as an oily residue.

Example IV

A mixture of 27 parts of A-methyl 1-(4-fluorophenyl)-3-(hydroxymethyl)-6-methyl-4-oxo-1,3,8-triazaspiro[4,5]decane-8-carboxylate, 43 parts of potassium hydroxide and 276 parts of 2-propanol is stirred and refluxed for 5.50 hours. The reaction mixture is evaporated. The residue is dissolved in 250 parts of water. The 2-propanol is further evaporated. The aqueous solution is stirred at 80° C. for 30 minutes at atmospheric pressure. The whole is allowed to cool to room temperature and the product is extracted with dichloromethane. The extract is washed successively with water and a dilute hydrochloric acid solution and decanted from some precipitated tar. The aqueous acid phase is separated, alkalized with a dilute sodium hydroxide solution and the product is extracted again with dichloromethane. The extract is washed with water, dried, filtered and evaporated. The oil residue is crystallized from 12 parts of acetonitrile, yielding 7.8 parts of A-1-(4-fluorophenyl)-6-methyl-1,3,8-triazaspiro[4,5]decan-4-one; mp. 156° C.

In a similar manner there is also prepared:
B-1-(4-fluorophenyl)-6-methyl-1,3,8-triazaspiro[4,5]decan-4-one; mp. 172.6° C.

Example V

To a stirred and cooled (below 5° C.) mixture of 16 parts of ethyl 1-(4-fluorophenyl)-4-oxo-1,3,8-triazaspiro[4,5]decane-8-carboxylate, 200 parts of dimethyl sulfoxide and 200 parts of benzene are added 3.5 parts of a sodium hydride dispersion 50%. After stirring for 1 hour at a temperature below 5° C., there are added dropwise 10 parts of iodomethane at this temperature. Upon completion, stirring is continued overnight at room temperature. The reaction mixture is poured onto water and the layers are separated. The aqueous phase is extracted with methylbenzene. The extract is washed with water, dried, filtered and evaporated, yielding 14.7 parts (88%) of ethyl 1-(4-fluorophenyl)-3-methyl-4-oxo-1,3,8-triazaspiro[4,5]decane-8-carboxylate as a residue.

In a similar manner there is also prepared:
ethyl 1-(4-fluorophenyl)-4-oxo-3-(phenylmethyl)-1,3,8-triazaspiro[4,5]decane-8-carboxylate as a residue.

Example VI

A mixture of 14.7 parts of ethyl 1-(4-fluorophenyl)-3-methyl-4-oxo-1,3,8-triazaspiro[4,5]decane-8-carboxylate, 16 parts of sodium hydroxide and 160 parts of 1-butanol is stirred and refluxed for 4 hours. The reaction mixture is evaporated and the residue is taken up in water. The product is extracted with trichloromethane. The extract is washed with water, dried, filtered and evaporated. The residue is crystallized from a mixture of 2,2'-oxybispropane and methanol, yielding 2.7 parts (23%) of 1-(4-fluorophenyl)-3-methyl-1,3,8-triazaspiro[4,5]decan-4-one.

In a similar manner there are also prepared:
1-(4-fluorophenyl)-1,3,8-triazaspiro[4,5]decan-4-one and
1-(4-fluorophenyl)-3-(phenylmethyl)-1,3,8-triazaspiro[4,5]decan-4-one monohydrochloride; mp. 185° C.

Example VII

A mixture of 221 parts of 4-fluorobenzeneacetonitrile, 700 parts of sodium methoxide solution 30% and 900 parts of dimethylbenzene is stirred for 5 minutes. Then there are added dropwise 309 parts of methyl 2-propanoate (exothermic reaction: temperature rises to 65° C.). Upon completion, stirring is continued overnight at reflux temperature. The methanol is distilled off till an internal temperature of 110° C. is reached. After cooling, 1000 parts of a hydrochloric acid solution 6 N are added dropwise and the whole is stirred and refluxed for 5 minutes. Upon cooling, the layers are separated. The organic phase is dried, filtered and evaporated. The residue is stirred and refluxed for 4 hours together with 500 parts of acetic acid, 500 parts of water and 500 parts of a hydrochloric acid solution. After cooling, the product is extracted with trichloromethane. The extract is washed successively with water, with a diluted sodium hydroxide solution and again with water till neutralization, dried, filtered and evaporated. The residue is crystallized from 2-propanol, yielding 134.5 parts of 1-(4-fluorophenyl)-4-oxocyclohexanecarbonitrile; mp. 91.8° C.

Following the same procedure and using equivalent amounts of the appropriate starting materials there are also prepared:
4-oxo-1-[4-(phenylmethoxy)phenyl]-1-cyclohexanecarbonitrile as a residue;
4-benzoyl-4-(4-fluorophenyl)cyclohexanone as a residue;
1-(2-naphthalenyl)-4-oxocyclohexanecarbonitrile as a residue;
4-oxo-1-(2-thienyl)cyclohexanecarbonitrile as a residue; and
4-oxo-1-(2-pyridinyl)-1-cyclohexanecarbonitrile; mp. 90.1° C.

Example VIII

A mixture of 65 parts of 4-oxo-1-[4-(phenylmethoxy)phenyl]-1-cyclohexanecarbonitrile, 15.7 parts of 1,2-ethanediol, 0.2 parts of 4-methylbenzenesulfonic acid and 360 parts of methylbenzene is stirred and refluxed overnight with water-separator. The reaction mixture is cooled, washed successively with water, with a sodium hydroxide solution 5% and again with water, dried, filtered and evaporated. The residue is crystallized from 2-propanol, yielding 33.5 parts (47%) of 8-[4-(phenylmethoxy)phenyl]-1,4-dioxaspiro[4,5]decane-8-carbonitrile.

In a similar manner there are also prepared:
8-(1,3-benzodioxol-5-yl)-1,4-dioxaspiro[4,5]decane-8carbonitrile as a residue; and
8-(4-fluorophenyl)-1,4-dioxaspiro[4,5]decane-8-carbonitrile; mp. 96.6° C.

Example IX

A mixture of 283.5 parts of 8-(4-methoxyphenyl)-1,4-dioxaspiro[4,5]decane-8-carbonitrile, 168 parts of potassium hydroxide and 1100 parts of 1,2-ethanediol is stirred and refluxed for 24 hours. The reaction mixture is cooled, poured onto water and filtered. The filtrate is acidified with a concentrated hydrochloric acid solution and the product is extracted with trichloromethane. The extract is washed with water, dried, filtered and evaporated. The residue is suspended in 2-propanol. The product is filtered off and dried, yielding 245 parts (83.8%) of 8-(4-methoxyphenyl)-1,4-dioxaspiro[4,5]decane-8-carboxylic acid.

In a similar manner there is also prepared:
8-(4-fluorophenyl)-1,4-dioxaspiro[4,5]decane-8-carboxylic acid as a residue.

Example X

To a stirred sodium methoxide solution, previously prepared starting from 1.3 parts of sodium in 160 parts of methanol, are added 13 parts of 1-(4-fluorophenyl)-4-oxocyclohexanecarboxylic acid and the whole is stirred and refluxed for 1 hour. After cooling to room temperature, 22.8 parts of iodomethane are added dropwise. Upon completion, the whole is heated to reflux and stirring is continued overnight at reflux temperature. The reaction mixture is evaporated and the residue is taken up in trichloromethane. The organic phase is washed successively with water, a 5% sodium hydroxide solution and again with water, dried, filtered and evaporated. The residue is purified by column-chromatography over silica gel using trichloromethane as eluent. The pure fractions are collected and the eluent is evaporated, yielding 5 parts (36%) of methyl 1-(4-fluorophenyl)-4-oxocyclohexanecarboxylate as an oily residue.

Following the same procedure and using equivalent amounts of the appropriate starting materials there are also prepared:
butyl 1-(4-fluorophenyl)-4-oxocyclohexanecarboxylate as a residue; and
propyl 1-(4-fluorophenyl)-4-oxocyclohexanecarboxylate.

Example XI

A mixture of 245 parts of 8-(4-methoxyphenyl)-1,4-dioxaspiro[4,5]decane-8-carboxylic acid, 150 parts of thionyl chloride and 1350 parts of benzene is stirred first for 30 minutes at room temperature and further for 4 hours at reflux. The reaction mixture is evaporated, yielding 275 parts of 8-(4-methoxyphenyl)-1,4-dioxaspiro[4,5]decane-8-carbonyl chloride as a residue.

In a similar manner there is also prepared: 8-(4-fluorophenyl)-1,4-dioxaspiro[4,5]decane-8-carbonyl chloride as a residue.

Example XII

To a stirred and cooled (<0° C.) mixture of 49.5 parts of N-methylmethanamine solution 40%, 93 parts of sodium carbonate and 1000 parts of water is added dropwise a solution of 124 parts of 8-(4-methoxyphenyl)-1,4-dioxaspiro[4,5]decane-8-carbonyl chloride in 675 parts of methylbenzene. Upon completion, stirring is continued overnight at room temperature. The layers are separated and the organic phase is washed with water, dried, filtered and evaporated, yielding 128 parts (100%) of 8-(4-methoxyphenyl)-N,N-dimethyl-1,4-dioxaspiro[4,5]decane-8-carboxamide as a residue.

Example XIII

To 120 parts of absolute ethanol is added dropwise a solution of 102 parts of 8-(4-fluorophenyl)-1,4-dioxaspiro[4,5]decane-8-carbonyl chloride in 270 parts of methylbenzene, while cooling. Upon completion, the whole is stirred for 24 hours at reflux temperature. The reaction mixture is cooled, washed with water, dried, filtered and evaporated, yielding 95 parts (90.6%) of ethyl 8-(4-fluorophenyl)-1,4-dioxaspiro[4,5]decane-8-carboxylate as a residue.

Example XIV

To a stirred mixture of 7.3 parts of magnesium and 350 parts of 1,1'-oxybisethane are added dropwise 43 parts of iodomethane under nitrogen atmosphere. The reaction is kept at reflux temperature in a water-bath. After refluxing for 30 minutes, 270 parts of benzene are added. The 1,1'-oxybisethane is distilled off till an internal temperature of 74° C. Then there is added a solution of 26 parts of 8-(4-fluorophenyl)-1,4-dioxaspiro[4,5]decane-8-carbonitrile in 45 parts of benzene. The whole is stirred and refluxed overnight. After cooling to room temperature, there is added dropwise a solution of 39 parts of hydrochloric acid in 100 parts of water (strongly exothermic). Upon completion, stirring is continued overnight at reflux temperature. The reaction mixture is cooled and the layers are separated. The aqueous phase is extracted with methylbenzene. The combined organic phases are washed with water, dried, filtered and evaporated. The residue is purified by column-chromatography over silica gel using trichloromethane as eluent. The pure fractions are collected and the eluent is evaporated. The oily residue is stirred with 150 parts of a hydrochloric acid solution 6 N and 150 parts of acetic acid. The whole is stirred for 24 hours at reflux. After cooling, the product is extracted with trichloromethane. The extract is washed with water, dried, filtered and evaporated. The residue is purified by column-chromatography over silica gel using trichlormethane as eluent. The pure fraction is collected and the eluent is evaporated, yielding 3.5 parts (15%) of 4-acetyl-4-(4-fluorophenyl)cyclohexanone as an oil residue.

Example XV

To a stirred and hot (±100° C.) mixture of 101 parts of sodium and 450 parts of methylbenzene is added dropwise a solution of 189 parts of 8-(4-fluorophenyl)-1,4-dioxaspiro[4,5]decane-8-carbonitrile in 450 parts of methylbenzene and 100 parts of absolute ethanol (temperature remained at about 90° C.). Then there are added successively and dropwise 260 parts of absolute ethanol and 160 parts of methanol. Upon completion, stirring is continued overnight at room temperature. The reaction mixture is poured onto ice-water and the product is extracted with trichloromethane. The extract is washed successively with a hydrochloric acid solution 5%, a sodium bicarbonate solution 5% and with water, dried, filtered and evaporated, yielding 167 parts of 8-(4-fluorophenyl)-1,4-dioxaspiro[4,5]decane; mp. <60° C.

In a similar manner there is also prepared:
8-(1,3-benzodioxol-5-yl)-1,4-dioxaspiro[4,5]decane as a residue.

Example XVI

To a stirred and heated (±65° C.) mixture of 60 parts of sodium amide solution 50% in dimethylbenzene and 315 parts of methylbenzene are added portionwise 33.5 parts of 8-[4-(phenylmethoxy)phenyl]-1,4-dioxaspiro[4,5]decane-8-carbonitrile. Upon completion, stirring is continued for 24 hours at reflux. The reaction mixture is cooled, about 16 parts of methanol are added dropwise and the whole is poured onto ice-water. The product is extracted with trichloromethane. The extract is dried, filtered and evaporated, yielding 27 parts (87%) of 8-[4-(phenylmethoxy)phenyl]-1,4-dioxaspiro[4,5]decane as a residue.

Example XVII

A mixture of 40 parts of 8-(4-fluorophenyl)-1,4-dioxaspiro[4,5]decane-8-carboxylic acid, 100 parts of a hydrochloric acid solution 6 N and 100 parts of acetic acid is started and refluxed overnight. The reaction mixture is cooled and the product is extracted with trichloromethane. The extract is washed three times with water, dried, filtered and evaporated, yielding 17 parts (50%) of 1-(4-fluorophenyl)-4-oxocyclohexanecarboxylic acid as a residue.

Example XVIII

A mixture of 95 part of ethyl 8-(4-fluorophenyl)-1,4-dioxaspiro[4,5decane-8-carboxylate, 66 parts of acetic acid, 34 parts of water and 180 parts of tetrahydrofuran is stirred and refluxed for 18 hours. The reaction mixture is cooled, poured onto water and the product is extracted with trichloromethane. The extract is washed successively with water, a sodium bicarbonate solution and again with water, dried, filtered and evaporated. The residue is distilled, yielding 11.3 parts (13.9%) of ethyl 1-(4-fluorophenyl)-4-oxocyclohexanecarboxylate; bp. 175°–185° C. at 2 mm. pressure.

Example XIX

A mixture of 160 parts of 8-(4-fluorophenyl)-1,4-dioxaspiro[4,5]decane, 72 parts of hydrochloric acid, 800 parts of ethanol and 800 parts of water is stirred and refluxed for 2 h. 30. Then there are added dropwise 72 parts of sulfuric acid. Upon completion, stirring is continued at reflux temperature for one hour. The reaction mixture is cooled, poured onto water and the product is extracted with trichloromethane. The extract is washed with water, dried, filtered and evaporated. The residue is fractionated, yielding 68.5 parts of 4-(4-fluorophenyl)-cyclohexanone; b.p. 110° C. at 1 mm. pressure.

In a similar manner there are also prepared:

4-[4-(phenylmethoxy)phenyl]-1-cyclohexanone as a residue;
4-(1,3-benzodioxol-5-yl)-1-cyclohexanone; mp. 102° C. and
1-(4-methoxyphenyl)-N,N-dimethyl-4-oxo-1-cyclohexanecarboxamide as a residue.

Example XX

To a stirred mixture of 75 parts of 4-(4-methoxyphenyl)cyclohexanol and 1000 parts of pyridine are added dropwise 62 parts of methanesulfonyl chloride (exothermic reaction: temperature rises to 40° C.). Upon completion, the whole is heated to 65° C. and stirring is continued for 2 hours, while meantime the mixture is allowed to cool to room temperature. The reaction mixture is evaporated and 1000 parts of water are added to the residue. The product is extracted with dichloromethane. The extract is washed with water, dried, filtered and evaporated. The residue is crystallized from 2-propanol, yielding 80.5 parts of 4-(4-methoxyphenyl)-cyclohexyl methanesulfonate.

Example XXI

A mixture of 7 parts of 4-phenylcyclohexanone, 8.8 parts of 1-(4-piperidinyl)-2H-benzimidazol-2-one, 0.3 parts of 4-methylbenzenesulfonic acid and 225 parts of methylbenzene is stirred and refluxed for 40 hours with water-separator. The reaction mixture is cooled and the solvent is removed in vacuo, yielding 15 parts of 1-[4-phenyl-1-cyclohexenyl)-4-piperidinyl]-2H-benzimidazol-2-one as a residue.

Following the same procedure and using equivalent amounts of the appropriate starting materials there are also prepared:
4-[4-(2,3-dihydro-2-oxo-1-H-benzimidazol-1-yl)-1-piperidinyl]-1-(4-fluorophenyl)-3-cyclohexene-1-carbonitrile as a residue;
1-(4-chlorophenyl)-4-[4-(2,3-dihydro-2-oxo-1H-benzimidazol-1-yl)-1-piperidinyl]-3-cyclohexene-1-carbonitrile as a residue;
1-(4-chlorophenyl)-4-[4-(2,3-dihydro-2-oxo-1H-benzimidazol-1-yl)-1-piperidinyl]-N,N-dimethyl-3-cyclohexenecarboxamide as a residue;
1,3-dihydro-1-[1-[4-[4-(phenylmethoxy)phenyl]-1-cyclohexenyl]-4-piperidinyl]-2H-benzimidazol-2-one as a residue; and
4-[4-(2,3-dihydro-2-oxo-1H-benzimidazol-1-yl)-1-piperidinyl]-1-(4-methoxyphenyl)-N,N-dimethyl-3-cyclohexenecarboxamide as a residue.

Example XXII

A mixture of 5 parts of 4-oxo-1-phenyl-1-cyclohexanecarbonitrile, 5.8 parts of 1-phenyl-1,3,8-triazaspiro[4,5]decan-4-one, 0.1 parts of 4-methylbenzenesulfonic acid and 225 parts of methylbenzene is stirred and refluxed overnight with water-separator. The reaction mixture is cooled and evaporated, yielding 10.35 parts of 4-(4-oxo-1-phenyl-1,3,8-triazaspiro[4,5]dec-8-yl)-1-phenyl-3-cyclohexene-1-carbonitrile as a residue.

Following the same procedure and using equivalent amounts of the appropriate starting materials there are also prepared:
1-phenyl-8-(4-phenyl-1-cyclohexenyl)-1,3,8-triazaspiro[4,5]-decan-4-one as a residue;
4-(4-oxo-1-phenyl-1,3,8-triazaspiro[4,5]dec-8-yl)-N,N-dimethyl-1-phenyl-3-cyclohexene-1-carboxamide as a residue;
1-(4-chlorophenyl)-4-(4-oxo-1-phenyl-1,3,8-triazaspiro[4,5]dec-8-yl)-3-cyclohexen-1-carbonitrile as a residue;
1-(4-fluorophenyl)-4-(4-oxo-1-phenyl-1,3,8-triazaspiro[4,5]dec-8-yl)-3-cyclohexene-1-carbonitrile as a residue; and
1-(4-methoxyphenyl)-4-(4-oxo-1-phenyl-1,3,8-triazaspiro[4,5]dec-8-yl)-3-cyclohexene-1-carbonitrile as a residue.

B. Preparation of Final Compounds

Example XXIII

To 1 part of a solution of 2 parts of thiophene in 40 parts of ethanol are added 3.2 parts of 4-(4-fluorophenyl)-4-hydroxy-1-cyclohexanone, 3.3 parts of 1,3-dihydro-1-(4-piperidinyl)-2H-benzimidazol-2-one and 200 parts of methanol. The whole is hydrogenated at normal pressure and at room temperature with 2 parts of palladium-on-charcoal catalyst 10%. After the calculated amount of hydrogen is taken up, the catalyst is filtered off over Hyflo and the filtrate is evaporated. The residue is converted into the hydrochloride salt in 2-propanol, 2,2'-oxybispropane and 2-propanone. The salt is filtered off and dried, yielding 2.8 parts (41.8%) of 1-[1-[4-(4-fluorophenyl)-4-hydroxycyclohexyl]-4-piperidinyl]1,3-dihydro-2H-benzimidazol-2-one hydrochloride; mp. >300° C.

Following the same reductive amination procedure and using equivalent amounts of the appropriate starting materials there are also prepared:

| $R^1$ | $Ar^1$ | base or salt form | mp. °C. |
|---|---|---|---|
| H | 4-F—$C_6H_4$ | base | 189.8 |
| $COOC_2H_5$ | 4-F—$C_6H_4$ | HCl | 263.2 |
| H | 1,3-benzodioxol-5-yl | base | 189.7 |
| H | 2-$CH_3O$—$C_6H_4$ | base | 252.8 |
| CN | $C_6H_5$ | HCl | 300.6 |
| $COOC_2H_5$ | $C_6H_5$ | base | 212.7 |

Example XXIV

To 1 part of a solution of 2 parts of thiophene in 40 parts of ethanol are added 2.2 parts of 1-(4-fluorophenyl)-4-oxocyclohexanecarbonitrile, 2.7 parts of 1-(4-fluorophenyl)-3-methyl-1,3,8-triazaspiro[4,5]decan-4-one and 90 parts of 2-methoxyethanol. The whole is hydrogenated at normal pressure and at 50° C. with 2 parts of palladium-on-charcoal catalyst 10%. After the calculated amount of hydrogen is taken up, the catalyst is filtered off and the filtrate is evaporated. The residue is purified by column-chromatography over silica gel using a mixture of trichloromethane and methanol (98:2 volume) as eluent. The first fraction (A-isomer) is collected and the eluent is evaporated. The residue is crystallized from a mixture of 2,2'-oxybispropane and methanol, yielding 0.5 parts (11%) of (A)-1-(4-fluorophenyl)-4-[1-(4-fluorophenyl)-3-methyl-4-oxo-1,3,8-triazaspiro[4,5]-dec-8-yl]cyclohexanecarbonitrile; mp. 187.1° C.

The second fraction (B-isomer) is collected and the eluent is evaporated. The residue is crystallized from a mixture of 2,2'-oxybispropane and methanol, yielding 3-(phenylmethyl)-1,3,8-triazaspiro[4,5]dec-8-yl]cyclohexanecarbonitrile; mp. 131° C.

Following the same reductive amination procedure and using equivalent amounts of the appropriate starting materials there are also prepared:

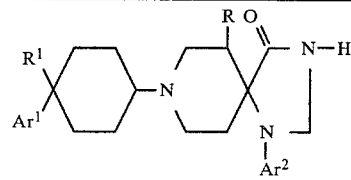

| $R^1$ | $Ar^1$ | $Ar^2$ | R | base or salt form | stereo-isomer | mp. °C. |
|---|---|---|---|---|---|---|
| H | 4-F—$C_6H_4$ | $C_6H_5$ | H | base | — | 234.5 |
| H | 3-$OCH_3$—$C_6H_4$ | $C_6H_5$ | H | base | — | 251.4 |
| $COOC_2H_5$ | 4F—$C_6H_4$ | $C_6H_5$ | H | base | — | 209.2 |
| CN | 4F-$C_6H_4$ | 4-F—$C_6H_4$ | H | base | B | 224.7 |
| COOH | $C_6H_5$ | 4-F—$C_6H_4$ | H | HCl | — | 287.8 |
| $COOC_2H_5$ | $C_6H_5$ | 4-F—$C_6H_4$ | H | base | — | 226.5 |
| CO—$C_6H_5$ | 4-F—$C_6H_4$ | 4-F—$C_6H_4$ | H | base | — | 219.1 |
| CN | 4-F—$C_6H_4$ | 4-F—$C_6H_4$ | H | base | Ac | 234.3 |
| OH | 4-F—$C_6H_4$ | 4-F—$C_6H_4$ | H | HCl | — | 268.8 |
| COOH | 4-F—$C_6H_4$ | 4-F—$C_6H_4$ | H | HCl . $H_2O$ | — | 282.8 |
| $COOC_2H_5$ | 4-F—$C_6H_4$ | 4-F—$C_6H_4$ | H | base | — | 214.5 |
| $COOCH_3$ | 4-F—$C_6H_4$ | 4-F—$C_6H_4$ | H | base | — | 221.5 |
| COOn . $C_4H_9$ | 4-F—$C_6H_4$ | 4-F—$C_6H_4$ | H | base | A − B | 174.5 |
| COOn . $C_3H_7$ | 4-F—$C_6H_4$ | 4-F—$C_6H_4$ | H | base | A + B | 188.7 |
| $OCH_3$ | 4-F—$C_6H_4$ | 4-F—$C_6H_4$ | H | base | A + B | 211–242 |
| CN | 4-F—$C_6H_4$ | 4-F—$C_6H_4$ | H | base | A + B | — |
| H | 4-$OCH_3$—$C_6H_4$ | $C_6H_5$ | H | base | — | 216.7 |
| CN | 2-naphthalenyl | 4F—$C_6H_4$ | H | base | B | 237.5 |
| CN | 2-thienyl | 4F—$C_6H_4$ | H | base | A + B | 184.3 |
| CN | 2-pyridinyl | 4F—$C_6H_4$ | H | base | — | 231.6 |
| CN | 1-naphthalenyl | 4F—$C_6H_4$ | H | base | B | 253.6 |
| CN | 4F—$C_6H_4$ | 4F—$C_6H_4$ | $CH_3$ | base | cis | 213.6 |
| CN | 4F—$C_6H_4$ | 4F—$C_6H_4$ | $CH_3$ | base | trans | 247.8 |

1.5 parts (33%) of (B)-1-(4-fluorophenyl)-4-[1-(4-fluorophenyl)-3-methyl-4-oxo-1,3,8-triazaspiro[4,5]dec-8-yl]cyclohexanecarbonitrile; mp. 158.5° C.

In a similar manner there are also prepared:
(A)-8-[4-acetyl-4-(4-fluorophenyl)cyclohexyl]-1-(4-fluorophenyl)-1,3,8-triazaspiro[4,5]decan-4-one monohydrochloride; mp. 258.9° C.; and
(B)-8-[4-acetyl-4-(4-fluorophenyl)cyclohexyl]-1-(4-fluorophenyl)-1,3,8-triazaspiro[4,5]decan-4-one monohydrochloride; mp. 286.0° C.

Example XXV

To 1 part of a solution of 2 parts of thiophene in 40 parts of ethanol are added 4.35 parts of 1-(4-fluorophenyl)-4-oxocyclohexanecarbonitrile, 6.3 parts of 1-(4-fluorophenyl)-3-(phenylmethyl)-1,3,8-triazaspiro[4,5decan-4-one monohydrochloride, 5 parts of potassium acetate and 100 parts of 2-methoxyethanol. The whole is hydrogenated at normal pressure and at 50° C. with 2 parts of palladium-on-charcoal catalyst 10%. After the calculated amount of hydrogen is taken up, the catalyst is filtered off and the filtrate is evaporated. The residue is taken up in water and the whole is alkalized with sodium hydroxide.

The product is extracted with trichloromethane. The extract is washed with water, dried, filtered and evaporated. The residue is crystallized from a mixture of 2,2'-oxybispropane and methanol. The product is filtered off and recrystallized from a mixture of 2,2'-oxybispropane and methanol, yielding 4.5 parts (49%) of (B)-1-(4-fluorophenyl)-4-[1-(4-fluorophenyl)-4-oxo-

Example XXVI

To a stirred mixture of 11 parts of 1-(4-chlorophenyl)-4-[4-(2,3-dihydro-2-oxo-1H-benzimidazol-1-yl)-1-piperidinyl]-3-cyclohexene-1-carbonitrile, 5 parts of sodium methoxide solution 30% and 320 parts of methanol are added portionwise 3 parts of sodium borohydride. Upon completion, stirring is continued first for one hour at reflux temperature and further overnight at room temperature. The reaction mixture is poured onto water. The precipitated product is filtered off and boiled in methanol. The product is filtered off and dried, yielding 5.3 parts of 1-(4-chlorophenyl)-4-[4-(2,3-dihydro-2-oxo-1H-benzimidazol-1-yl)-1-piperidinyl]cyclohexanecarbonitrile; mp. 299° C.

Following the same reduction procedure there are also prepared:

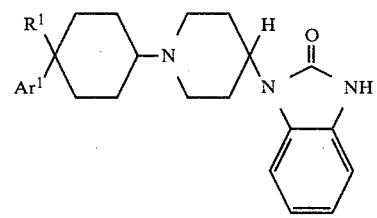

| $R^1$ | $Ar^1$ | base or salt form | mp. °C. |
|---|---|---|---|
| H | $C_6H_5$ | base | +300 |
| CN | 4-F—$C_6H_4$ | base | 285.4 |

-continued

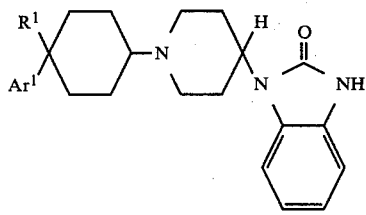

| R¹ | Ar¹ | base or salt form | mp. °C. |
|---|---|---|---|
| CON(CH₃)₂ | 4-Cl—C₆H₄ | i, C₃H₇OH | 281 |
| H | 4-(C₆H₅CH₂O)—C₆H₄ | HCl | +300 (dec.) |
| CON(CH₃)₂ | 4-OCH₃—C₆H₄ | HCl . H₂O | 286.2 |

Example XXVII

To a stirred mixture of 10.5 parts of 1-(4-fluorophenyl)-4-(4-oxo-1-phenyl-1,3,8-triazaspiro[4,5]dec-8-yl)-3-cyclohexene-1-carbonitrile, 1 part of sodium methoxide solution 30% and 320 parts of ethanol is added portionwise 1 part of sodium borohydride. Upon completion, starting at room temperature is continued for 6 hours. The reaction mixture is poured onto water and the product is extracted with trichloromethane. The extract is dried, filtered and evaporated. The residue is purified by column-chromatography over silica gel using a mixture of trichloromethane and 5% of methanol as eluent. The pure fractions are collected and the eluent is evaporated. The residue is crystallized from a mixture of methanol and 2-propanone, yielding 3.2 parts of 1-(4-fluorophenyl)-4-(4-oxo-1-phenyl-1,3,8-triazaspiro[4,5]dec-8-yl)cyclohexanecarbonitrile; mp. 236.1° C.

Following the same reduction procedure there are also prepared:

| R¹ | Ar¹ | Ar² | R⁴ | base or salt form | stereo-isomer | mp. °C. |
|---|---|---|---|---|---|---|
| H | C₆H₅ | C₆H₅ | H | base | — | 212.7 |
| CN | C₆H₅ | C₆H₅ | H | base | — | 236.1 |
| CON(CH₃)₂ | C₆H₅ | C₆H₅ | H | HCl | — | 268.4 |
| CN | 4-Cl—C₆H₄ | C₆H₅ | H | base | — | +300 |
| CN | 4-OCH₃C₆H₄ | C₆H₅ | H | base | — | 235.4 |

Example XXVIII

A mixture of 4.34 parts of 1,3-dihydro-1-(4-piperidinyl)-2H-benzimidazol-2-one, 10.6 parts of sodium carbonate and 120 parts of 4-methyl-2-pentanone is distilled azeotropically to dry. Then there are added 6.25 parts of 4-(4-methoxyphenyl)cyclohexanol methanesulfonate and the whole is stirred and refluxed for 72 hours. After cooling, the reaction mixture is poured onto water and the layers are separated. The organic phase is dried, filtered and evaporated. The residue is crystallized twice from 2-propanol, yielding 0.4 parts of 1,3-dihydro-1-[1-[4-(4-methoxyphenyl)cyclohexyl]-4-piperidinyl]-2H-benzimidazol-2-one hemi-2-propanolate; mp. 167.6° C.

Example XXIX

To 27.6 parts of concentrated sulfuric acid are added portionwise 3 parts of (Ac)-1-(4-fluorophenyl)-4-[1-(4-fluorophenyl)-4-oxo-1,3,8-triazaspiro[4,5]decan-8-yl]cyclohexanecarbonitrile (slightly exothermic reaction). Upon completion, stirring is continued overnight at room temperature. The reaction mixture is poured onto ice-water. The precipitated product is filtered off, washed with water and stirred in a 10% sodium hydroxide solution. The product is extracted with trichloromethane. The extract is washed with water, dried, filtered and evaporated. The residue is crystallized from methanol, yielding 2.5 parts (80%) of (A)-1-(4-fluorophenyl)-4-[1-(4-fluorophenyl)-4-oxo-1,3,8-triazaspiro[4,5]dec-8-yl]cyclohexanecarboxamide methanolate (1:1).

To 36 parts of a sulfuric acid solution 97% are added portionwise 4.5 parts of (B)-1-(4-fluorophenyl)-4-[1-(4-fluorophenyl)-4-oxo-1,3,8-triazaspiro[4,5]decan-8-yl]cyclohexanecarbonitrile (slightly exothermic reaction). Upon completion, stirring is continued overnight at room temperature. The reaction mixture is poured onto ice-water. The precipitated product is filtered off, washed with water and stirred in a 5% sodium hydroxide solution in water. The product is filtered off and boiled in 200 parts of water. It is filtered off again and suspended in methylbenzene. The whole is evaporated and the residue is boiled in methanol. The product is filtered off and dried, yielding 2.3 parts (49%) of (B)-1-(4-fluorophenyl)-4-[1-(4-fluorophenyl)-4-oxo-1,3,8-triazaspiro[4,5]dec-8-yl]cyclohexanecarboxamide; mp. 271.7° C.

Example XXX

A mixture of 4.5 parts of (B)-1-(4-fluorophenyl)-4-[1-(4-fluorophenyl)-4-oxo-1,3,8-triazaspiro[4,5]-decan-8-yl]cyclohexanecarbonitrile, 1 part of 2-propenenitrile, 0.5 parts of N,N,N,-trimethylbenzenemethanaminimum hydroxide solution 40% in methanol and 200 parts of 1,4-dioxane is stirred and heated overnight at 60° C. The reaction mixture is evaporated. The residue is taken up in trichloromethane. The whole is washed with water, dried, filtered and evaporated. The residue is crystallized from methanol. The product is filtered off and dried for 24 hours at 120° C., yielding 4.6 parts (91%) of (B)-8-[4-cyano-4-(4-fluorophenyl)cyclohexyl]-1-(4-fluorophenyl)-4-oxo-1,3,8-triazaspiro[4,5]decane-3-propanenitrile; mp. 212.1° C.

In a similar manner there are also prepared:

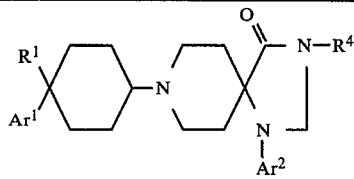

| R[1] | Ar[1] | Ar[2] | R[4] | base or salt form | stereo-isomer | mp. °C. |
|---|---|---|---|---|---|---|
| CN | 4-F—C6H4 | 4-F—C6H4 | CH2—CH2COOCH3 | HCl | H | 249.2 |
| CN | 4-F—C6H4 | 4-F—C6H4 | CH2CH(CH3)CN | base | B | 144.8 |
| CN | 4-F—C6H4 | 4-F—C6H4 | CH(CH3)CH2COOCH3 | HCl | B | 248.6 |
| CN | 4-F—C6H4 | 4-F—C6H4 | CH2CH2COCH3 | HCl . H2O | B | 241.1 |
| CN | 4-F—C6H4 | 4-F—C6H4 | CH2CH(CH3)—COOCH3 | HCl | B | 239.5 |
| CN | 4-F—C6H4 | 4-F—C6H4 | CH(CH3)CH2CN | base | B | 180.8 |

Example XXXI

A mixture of 4.5 parts of (B)-1-(4-fluorophenyl)-4-[1-(4-fluorophenyl)-4-oxo-1,3,8-trizaspiro[4,5]decan-8-yl]cyclohexanecarbonitrile, 2.5 parts of 2-bromopropane, 2.25 parts of potassium hydroxide and 100 parts of dimethyl sulfoxide is stirred overnight at room temperature. The reaction mixture is poured onto water. The precipitated product is filtered off, washed with water and dissolved in trichloromethane. The solution is dried, filtered and evaporated. The residue is crystallized from a mixture of 2,2'-oxybispropane and methanol, yielding 1.3 parts (26%) of (B)-1-(4-fluorophenyl)-4-[1-(4-fluorophenyl)-3-(1-methylethyl)-4-oxo-1,3,8-triazaspiro[4,5]dec-8-yl]cyclohexanecarbonitrile; mp. 157.5° C.

In a similar manner there are also prepared:

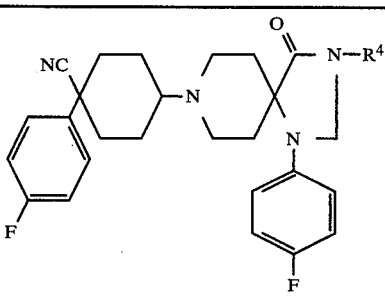

| R[4] | base or salt form | stereo isomer | mp. °C. |
|---|---|---|---|
| C2H5 | base | B | 168.3 |
| CH2CN | base | B | 209.5 |
| n . C4H9 | HCl | B | 273.0 |
| n . C4H9 | HCl | A | 220.8 |
| CH2—CH2—NH—COOC2H5 | base | B | 161.7 |
| CH2OCH3 | base | B | 155.7 |
| CO—C6H5 | base | B | 179.2 |
| CH2—CO—NH2 | base | B | 201.1 |
| CH2—CH2—CH2—CN | base | B | 122.6 |
| CH2—CO—NH—CH3 | HCl | B | 264-273 |
| CH2—CO—N(CH3)2 | HCl | B | 270-285 |

Example XXXII

A mixture of 4.5 parts of (B)-1-(4-fluorophenyl)-4-[1-(4-fluorophenyl)-4-oxo-1,3,8-triazaspiro[4,5]decan-8-yl]-cyclohexanecarbonitrile, 4 parts of acetic acid anhydride, 0.1 parts of 4-methylbenzenesulfonic acid and 360 parts of methylbenzene is stirred and refluxed for 24 hours. The reaction mixture is evaporated. The residue is purified by column-chromatography over silica gel using a mixture of trichloromethane and methanol (99:1 by volume) as eluent. The pure fractions are collected and the eluent is evaporated. The residue is stirred in 2,2'-oxybispropane. The product is filtered off and dried, yielding 1.6 parts (33%) of (B)-3-acetyl-8-[4-cyano-4-(4-fluorophenyl)cyclohexyl]-1-(4-fluorophenyl)-1,3,8-triazaspiro[4,5]decan-4-one; mp. 166.4° C.

Example XXXIII

A mixture of 4.5 parts of (B)-1-(4-fluorophenyl)-4-[1-(4-fluorophenyl)-4-oxo-1,3,8-triazaspiro[4,5]decan-8-yl]cyclohexanecarbonitrile, 2.2 parts of isothiocyanathomethane, 1 part of N,N-dimethyl-4-pyridinamine and 360 parts of methylbenzene is stirred and refluxed for 48 hours. The reaction mixture is evaporated. The residue is purified by column-chromatography over silica gel using a mixture of trichloromethane and methanol (99:1 by volume) as eluent. The pure fractions are collected and the eluent is evaporated. The residue is crystallized from 2-propanone, yielding 0.7 parts (13%) of (B)-8-[4-cyano-4-(4-fluorophenyl)cyclohexyl]-1-(4-fluorophenyl)-N-methyl-4-oxo-1,3,8-triazaspiro[4,5]-decane-3-carbothioamide; mp. 187.8° C.

Example XXXIV

A mixture of 4.5 parts of (B)-1-(4-fluorophenyl)-4-[1-(4-fluorophenyl)-4-oxo-1,3,8-triazaspiro[4,5]decan-8-yl]cyclohexanecarbonitrile, 3.6 parts of isocyanatobenzene, 1 part of N,N-dimethyl-4-pyridinamine and 195 parts of dichloromethane is stirred and refluxed overnight. The reaction mixture is evaporated. The residue is purified by column-chromatography over silica gel using trichloromethane as eluent. The pure fractions are collected and the eluent is evaporated. The residue is crystallized from 2-propanone, yielding 3.5 parts (61%) of (B)-8-[4-cyano-4-(4-fluorophenyl)cyclohexyl]-1-(4-fluorophenyl)-4-oxo-N-phenyl-1,3,8-triazaspiro[4,5]-decane-3-carboxamide; mp. 118.8° C.

Example XXXV

A mixture of 5 parts of (B)-ethyl [2-[8-[4-cyano-4-(4-fluorophenyl)cyclohexyl]-1-(4-fluorophenyl)-4-oxo-1,3,8-triazaspiro[4,5]dec-3-yl]ethyl]carbamate, 5.6 parts of potassium hydroxide and 240 parts of ethanol is stirred for 24 hours at reflux temperature. The reaction mixture is evaporated and the residue is stirred with water and dichloromethane. The organic phase is washed with water, dried, filtered and evaporated. The residue is purified by column-chromatography over silica gel using first a mixture of trichloromethane and methanol (97:3 by volume) and then a mixture of trichloromethane and methanol (90:10 by volume) as eluent. The pure fractions are collected and the eluent is evaporated. The residue is further purified by column-chromatography over silica gel using a mixture of trichloromethane and methanol (97:3 by volume), saturated with ammonia, as eluent. The pure fractions are collected and the eluent is evaporated. The residue is converted into the hydrochloride salt in methanol. The salt is filtered off and dried, yielding 1 part (54%) of (B)-4-[3-(2-aminoethyl)-1-(4-fluorophenyl)-4-oxo-1,3,8-triazaspiro[4,5]dec-8-yl]-1-(4-fluorophenyl)cyclohexanecarbonitrile dihydrochloride. dihydrate; mp. 247.8° C.

What is claimed is:

1. A chemical compound represented by the formula

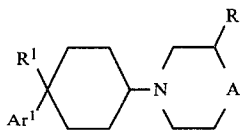  (I)

the pharmaceutically acceptable acid addition salts and the stereochemically isomeric forms thereof, wherein $Ar^1$ is a member selected from the group consisting of aryl and 1,3-benzodioxolyl;

R is a member selected from the group consisting of hydrogen and lower alkyl;

$R^1$ is a member selected from the group consisting of hydrogen, cyano, carboxyl, lower alkyloxycarbonyl, aryllower alkyloxycarbonyl, aminocarbonyl, mono- and di(lower alkyl)aminocarbonyl, mono- and di(aryllower alkyl)aminocarbonyl, (aryllower alkyl)lower alkylamino-carbonyl, hydroxy, lower alkyloxy, lower alkylcarbonyloxy, formyl, lower alkylcarbonyl, arylcarbonyl, aryllower alkylcarbonyl, lower alkyl, lower alkenyl, lower alkynyl and cyclohexyl; and A has the formula

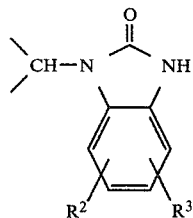  (a)

wherein $R^2$ and $R^3$ are each independently selected from the group consisting of hydrogen, halo, trifluoromethyl, lower alkyl and lower alkyloxy; or A has the formula

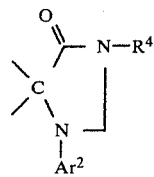  (b)

wherein $Ar^2$ is aryl, and $R^4$ is a member selected from the group consisting of hydrogen, lower alkyl, aryllower alkyl, cyano-lower alkyl, aminolower alkyl, mono- and di(lower alkyl)aminolower alkyl, mono- and di(aryllower alkyl)amino-lower alkyl, lower alkyl, hydroxylower alkyl, mercaptolower alkyl, lower alkyloxy-lower alkyl, lower alkylthiolower alkyl, aryloxylower alkyl, arylthiolower alkyl, aryllower alkyloxylower alkyl, aryllower alkylthiolower alkyl, and a radical of formula

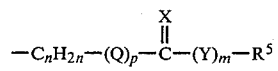

wherein n is 0 or an integer of from 1 to 6 inclusive, Q is O, S or $NR^6$, p is 0 or 1, X is O or S, $R^5$ is hydrogen, lower alkyl, aryl or aryllower alkyl, m is 0 or 1 and Y is O, S or $NR^6$, wherein $R^6$ as used in the definition of Q and Y is hydrogen, lower alkyl, aryl or aryllower alkyl:

provided that when Y is O and m and p are each 1 than $R^5$ is other than hydrogen and provided that when p is 1 than n is other than 0;

wherein aryl, whether used alone or as a portion of another term, is a member selected from the group consisting of phenyl, thienyl, pyridinyl, naphthalenyl and substituted phenyl, said substituted phenyl having from 1 to 3- substituents each independently selected from the group consisting of halo, lower alkyl, lower alkyloxy, phenyl lower alkyloxy, trifluoromethyl, nitro, amino and hydroxy.

2. A chemical compound according to claim 1 wherein A has the formula

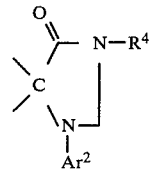

3. A chemical compound selected from the group consisting of (B)-8-[4-cyano-4-(4-fluorophenyl)cyclohexyl]-1-(4-fluorophenyl)-α-methyl-4-oxo-1,3,8-triazaspiro[4,5]decane-3-propanenitrile and the pharmaceutically acceptable acid addition salts thereof.

4. A chemical compound selected from the group consisting of (B)-8-[4-cyano-4-(4-fluorophenyl)cyclohexyl]-1-(4-fluorophenyl)-4-oxo-1,3,8-triazaspiro[4,5]decane-3-acetamide and the pharmaceutically acceptable acid addition salts thereof.

5. A pharmaceutical composition in dosage unit form comprising per dosage unit an effective antiemetic or psychotropic amount of a compound represented by the formula

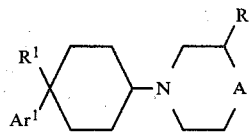

the pharmaceutically acceptable acid addition salts and the stereo-chemically isomeric forms thereof, wherein Ar$^1$ is a member selected from the group consisting of aryl and 1,3-benzodioxolyl;

R is a member selected from the group consisting of hydrogen and lower alkyl;

R$^1$ is a member selected from the group consisting of hydrogen, cyano, carboxyl, lower alkyloxycarbonyl, aryllower alkyloxycarbonyl, aminocarbonyl, mono- and di(lower alkyl)aminocarbonyl, mono- and di(aryllower alkyl)aminocarbonyl, (aryllower alkyl)lower alkylamino-carbonyl, hydroxy, lower alkyloxy, lower alkylcarbonyloxy, formyl, lower alkylcarbonyl, arylcarbonyl, aryllower alkylcarbonyl, lower alkyl, lower alkenyl, lower alkynyl and cyclohexyl; and A has the formula

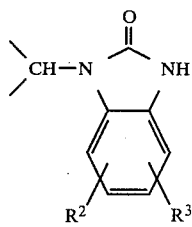

wherein R$^2$ and R$^3$ are each independently selected from the group consisting of hydrogen, halo, trifluoromethyl, lower alkyl and lower alkyloxy; or A has the formula

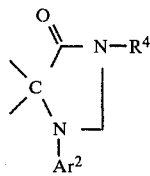

wherein Ar$^2$ is aryl, and

R$^4$ is a member selected from the group consisting of hydrogen, lower alkyl, aryllower alkyl, cyanolower alkyl, aminolower alkyl, mono- and di(lower alkyl)aminolower alkyl, mono- and di(aryllower alkyl)-aminolower alkyl, lower alkyl, hydroxylower alkyl, mercaptolower alkyl, lower alkyloxylower alkyl, lower alkylthiolower alkyl, aryloxylower alkyl, arylthiolower alkyl, aryllower alkyloxylower alkyl, aryllower alkylthiolower alkyl, and a radical of formula

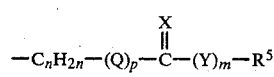

wherein n is o or an integer of from 1 to 6 inclusive, Q is O, S or NR$^6$, p is o or 1, X is O or S, R$^5$ is hydrogen, lower alkyl, aryl or aryllower alkyl, m is o or 1 and Y is O, S or NR$^6$, wherein R$^6$ as used in the definition of Q and Y is hydrogen, lower alkyl, aryl or aryllower alkyl; provided that when Y is O and m and p are each 1 than R$^5$ is other than hydrogen and provided than when p is 1 than n is other than o;

wherein aryl, whether used alone or as a portion of another term, is a member selected from the group consisting of phenyl, thienyl, pyridinyl, naphthalenyl and substituted phenyl, said substituted phenyl having from 1 to 3 substituents each independently selected from the group consisting of halo, lower alkyl, lower alkyloxy, phenyl lower alkyloxy, trifluoromethyl, nitro, amino and hydroxy.

6. A pharmaceutical composition according to claim 5 wherein A has the formula

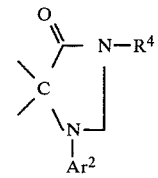

7. A pharmaceutical composition in dosage unit form comprising per dosage unit an effective antiemetic or psychotropic amount of a compound selected from the group consisting of (B)-8-[4-cyano-4-(4-fluorophenyl)-cyclohexyl]-1-(4-fluorophenyl)-α-methyl-4-oxo-1,3,8-triazaspiro[4,5]decane-3-propanenitrile and the pharmaceutically acceptable acid addition salts thereof.

8. A pharmaceutical composition in dosage unit form comprising per dosage unit an effective antiemetic or psychotropic amount of a compound selected from the group consisting of (B)-8-[4-cyano-4-(4-fluorophenyl)-cyclohexyl]-1-(4-fluorophenyl)-4-oxo-1,3,8-triazaspiro[4,5]decane-3-acetamide and the pharmaceutically acceptable acid addition salts thereof.

9. A method of inhibiting emesis or mental disorders which comprise the systemic administration to warm-blooded animals of an effective antiemetic or psychotropic amount of a compound represented by the formula

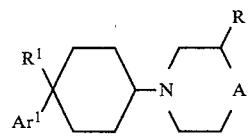

the pharmaceutically acceptable acid addition salts and the stereo-chemically isomeric forms thereof, wherein Ar$^1$ is a member selected from the group consisting of aryl and 1,3-benzodioxolyl;

R is a member selected from the group consisting of hydrogen and lower alkyl;

R$^1$ is a member selected from the group consisting of hydrogen, cyano, carboxyl, lower alkyloxycarbonyl, aryllower alkyloxycarbonyl, aminocarbonyl, mono- and di(lower alkyl)aminocarbonyl, mono- and di(aryllower alkyl)aminocarbonyl, (aryllower alkyl)lower alkylamino- carbonyl, hydroxy, lower alkyloxy, lower alkylcarbonyloxy, formyl, lower alkylarbonyl, arylcarbonyl, aryllower alkylcarbonyl, lower alkyl, lower alkenyl, lower alkynyl and cyclohexyl; and A has the formula

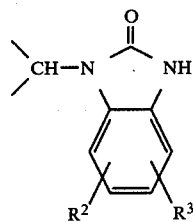
(a)

wherein $R^2$ and $R^3$ are each independently selected from the group consisting of hydrogen, halo, trifluoromethyl, lower alkyl and lower alkyloxy; or A has the formula

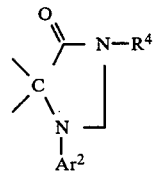
(b)

wherein $Ar^2$ is aryl, and
$R^4$ is a member selected from the group consisting of hydrogen, lower alkyl, aryllower alkyl, cyanolower alkyl, aminolower alkyl, mono- and di(lower alkyl)aminolower alkyl, mono- and di(aryllower alkyl)-aminolololower alkyl, lower alkyl, hydroxylower alkyl, mercaptolower alkyl, lower alkyloxylower alkyl, lower alkylthiolower alkyl, aryloxylower alkyl, arylthiolower alkyl, aryllower alkyloxylower alkyl, aryllower alkylthiolower alkyl, and a radical of formula

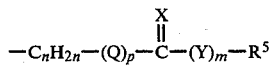

wherein n is o or an integer of from 1 to 6 inclusive, Q is O, S or $NR^6$, p is o or 1, X is O or S, $R^5$ is hydrogen, lower alkyl, aryl or aryllower alkyl, m is o or 1 and Y is O, S or $NR^6$, wherein $R^6$ as used in the definition of Q and Y is hydrogen, lower alkyl, aryl or aryllower alkyl; provided that when Y is O and m and p are each 1 than $R^5$ is other than hydrogen and provided that when p is 1 than n is other than o;

wherein aryl, whether used alone or as a portion of another term, is a member selected from the group consisting of phenyl, thienyl, pyridinyl, naphthalenyl and substituted phenyl, said substituted phenyl having from 1 to 3 substituents each independently selected from the group consisting of halo, lower alkyl, lower alkyloxy, phenyl lower alkyloxy, trifluoromethyl, nitro, amino and hydroxy.

10. A method of inhibiting emesis or mental disorders according to claim 9 wherein A has the formula

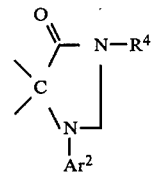

11. A method of inhibiting emesis or mental disorders which comprises the systemic administration to warm-blooded animals of an effective antiemetic or psychotropic amount of a compound selected from the group consisting of (B)-8-[4-cyano-4-(4-fluorophenyl)cyclohexyl]-1-(4-fluorophenyl)-α-methyl-4-oxo-1,3,8-triazaspiro[4,5]decane-3-propanenitrile and the pharmaceutically acceptable acid addition salts thereof.

12. A method of inhibiting emesis or mental disorders which comprises the systemic administration to warm-blooded animals of an effective antiemetic or psychotropic amount of a compound selected from the group consisting of (B)-8-[4-cyano-4-(4-fluorophenyl)cyclohexyl]-1-(4-fluorophenyl)-4-oxo-1,3,8-triazaspiro[4,5]decane-3-acetamide and the pharmaceutically acceptable acid addition salts thereof.

* * * * *

UNITED STATES PATENT AND TRADEMARK OFFICE
CERTIFICATE OF CORRECTION

PATENT NO. : 4,329,353     Page 1 of 2
DATED     : May 11, 1982
INVENTOR(S) : Raymond A. Stokbroekx, et al.

It is certified that error appears in the above—identified patent and that said Letters Patent is hereby corrected as shown below:

Claim 1: after formula 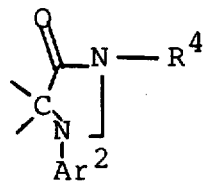

line 5, after the words "alkyl)amino-lower alkyl, insert -- [(aryllower alkyl)lower alkylamino] --

Claim 5: after formula 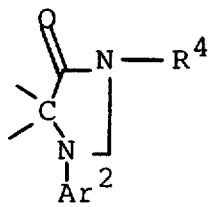

line 53, after the words "aminolower alkyl," insert -- [(aryllower alkyl)lower alkylamino] --

UNITED STATES PATENT AND TRADEMARK OFFICE
CERTIFICATE OF CORRECTION

PATENT NO. : 4,329,353
DATED : May 11, 1982
INVENTOR(S) : Raymond A. Stokbroekx, et al.

It is certified that error appears in the above—identified patent and that said Letters Patent is hereby corrected as shown below:

Claim 9. after formula 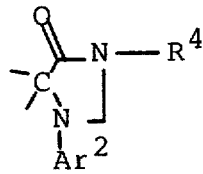

line 30, the word "aminololower" incorrect - should be -- aminolower -- and after the word "alkyl" should be -- [(aryllower alkyl)lower alkylamino] --.

Signed and Sealed this

Ninth Day of August 1983

[SEAL]

Attest:

Attesting Officer

GERALD J. MOSSINGHOFF

Commissioner of Patents and Trademarks